(12) United States Patent
Bruestle et al.

(10) Patent No.: US 10,470,741 B2
(45) Date of Patent: Nov. 12, 2019

(54) ULTRASOUND TRANSDUCER FOR IMAGING SYSTEMS

(71) Applicant: General Electric Company, Schenectady, NY (US)

(72) Inventors: Reinhold Bruestle, Zipf (AT); Jean-Francois Gelly, Sophia-Antipolis (FR); Bruno Hans Haider, Niskayuna, NY (US)

(73) Assignee: General Electric Company, Schenectady, NY (US)

( * ) Notice: Subject to any disclaimer, the term of this patent is extended or adjusted under 35 U.S.C. 154(b) by 886 days.

(21) Appl. No.: 15/087,417

(22) Filed: Mar. 31, 2016

(65) Prior Publication Data

US 2017/0281128 A1    Oct. 5, 2017

(51) Int. Cl.
*A61B 8/00* (2006.01)

(52) U.S. Cl.
CPC .......... *A61B 8/4477* (2013.01); *A61B 8/4488* (2013.01); *A61B 2562/12* (2013.01)

(58) Field of Classification Search
CPC ....... A61B 8/00; A61B 8/4477; A61B 8/4488; A61B 2562/12
See application file for complete search history.

(56) References Cited

U.S. PATENT DOCUMENTS

| | | | | |
|---|---|---|---|---|
| 4,546,771 | A   * | 10/1985 | Eggleton | A61B 8/12 348/163 |
| 7,594,439 | B2 * | 9/2009  | Fischer  | G01N 29/07 73/626 |
| 8,450,910 | B2   | 5/2013  | Gelly et al. | |
| 9,510,806 | B2 * | 12/2016 | Smith    | A61B 8/4461 |
| 9,572,549 | B2 * | 2/2017  | Belevich | A61B 8/587 |
| 9,668,714 | B2 * | 6/2017  | Call     | G01S 15/8952 |
| 2012/0065509 | A1 | 3/2012 | Ziv-Ari et al. | |

* cited by examiner

*Primary Examiner* — Joel Lamprecht

(74) *Attorney, Agent, or Firm* — Dean D. Small; The Small Patent Law Group, LLC

(57) ABSTRACT

A transducer array for an ultrasound probe is provided. The transducer array includes a plurality of transducer elements. Each of the transducer elements have an acoustic stack configured to generate ultrasound signals. The transducer array includes a front layer having a base and a transmission surface. The front layer is mounted to the acoustic stacks of the plurality or transducer elements. The transmission surface includes a linear incline. The transmission surface is configured to emit the ultrasound signals.

20 Claims, 9 Drawing Sheets

ULTRASOUND TRANSDUCER FOR IMAGING SYSTEMS

FIELD

Embodiments described herein generally relate to providing a front layer of an ultrasound transducer used in a diagnostic medical imaging system.

BACKGROUND OF THE INVENTION

Diagnostic medical imaging systems typically include a scan portion and a control portion having a display. For example, ultrasound imaging systems usually include ultrasound scanning devices, such as ultrasound probes having transducers that are connected to an ultrasound system to control the acquisition of ultrasound data by performing various ultrasound scans (e.g., imaging a volume or body). The ultrasound systems are controllable to operate in different modes of operation to perform the different scans. The signals received at the probe are then communicated and processed at a back end.

Conventional ultrasound probes include a plurality of acoustic stacks arranged in one or two dimensional (2D) arrays. The acoustic stacks transmit ultrasound signals to a body of interest. A front layer or lens is overlaid on each of the acoustic stacks. The front layer is typically a uniform curved concave or convex structure configured to focus the ultrasound signals received from the acoustic stack to a focal point normal to an imaging plane of the ultrasound probe. Additionally, based on the shape of the front layer artifact or reflection signals are focused and received by the front layer. For example, reflected signals from the body at the region of interest are partially reflected back as a lens echo or double pinning by the acoustic stack and the front layer back to the focal point. Additionally, due to the uniform structure of the front layer, the reflected signals of the lens echoes are temporally the same, which form a constructive signal through the body of interest. In another example, a portion of the ultrasound signals are reflected by the front layer creating a lens reflection that is transmitted back to the focal point. Since the lens echo and the constructive signals of the transducer reflection are focused by the front layer, at least a portion of the reflections of the lens echo and the transducer reflection are received along the imaging plane of the ultrasound probe. Thereby, creating distortions that are present in the reconstructed ultrasound image.

Therefore, a need exists for an improved front layer of an acoustic stack used within an ultrasound probe.

BRIEF DESCRIPTION OF THE INVENTION

In an embodiment, a transducer array for an ultrasound probe is provided. The transducer array includes a plurality of transducer elements. Each of the transducer elements have an acoustic stack configured to generate ultrasound signals. The transducer array includes a front layer having a base and a transmission surface. The front layer is mounted to the acoustic stacks of the plurality or transducer elements. The transmission surface includes a linear incline. The transmission surface is configured to emit the ultrasound signals.

In another embodiment a system (e.g., ultrasound imaging system) is provided. The system includes an ultrasound probe that has a housing. The system also includes a transducer array formed by a plurality of transducer elements. Each of the transducer elements have an acoustic stack configured to generate ultrasound signals. The transducer array includes a front layer enclosed within the housing. The front layer is mounted to the acoustic stacks. The front layer includes a base and a transmission surface. The transmission surface includes a linear incline. The transmission surface is configured to emit the ultrasound signals.

In another embodiment a method for manufacturing a front layer for an ultrasound transducer array is provided. The method includes providing a front layer. The front layer includes a base and a transmission surface. The transmission surface includes a linear incline. The method also includes mounting the front layer to a plurality of acoustic stacks. The acoustic stacks are configured to generate ultrasound signals. The transmission surface is configured to emit the ultrasound signals. The method also includes enclosing the front layer and the acoustic stack within a housing of an ultrasound probe.

DETAILED DESCRIPTION OF THE INVENTION

Figure 1:
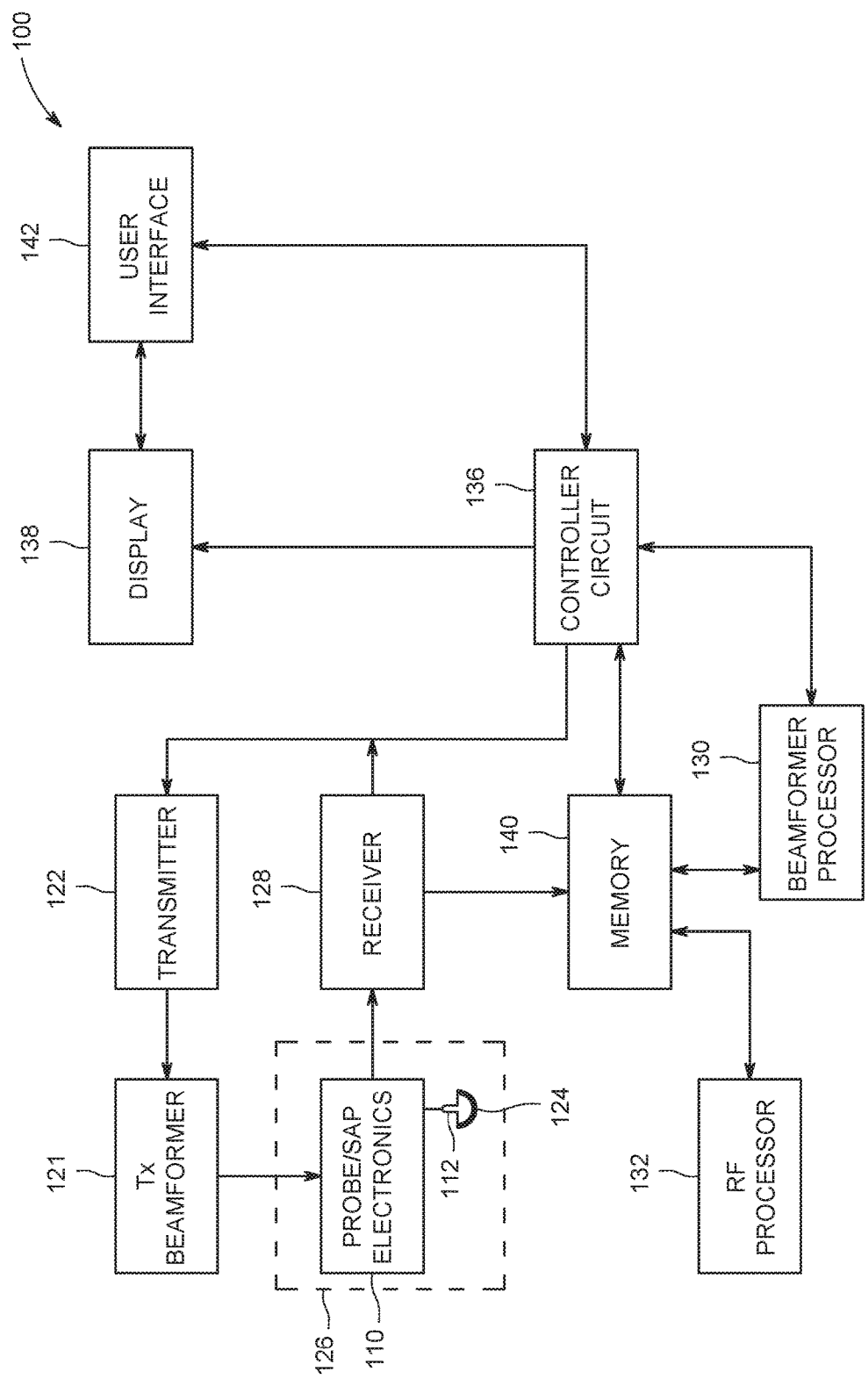
FIG. 1 illustrates a schematic block diagram of an ultrasound imaging system, in accordance with an embodiment.

The following detailed description of certain embodiments will be better understood when read in conjunction with the appended drawings. To the extent that the figures illustrate diagrams of the functional modules of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like). Similarly, the programs may be stand-alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Various embodiments provide systems and methods for a front layer of an ultrasound transducer. The front layer extends along a length of an acoustic transducer having a pair of opposing edges with different heights forming a wedge shape. For example, the front layer tapers to one of the opposing edges to form a linear slope or incline from a first edge to a second opposing edge. The change in thickness of the front layer is based on the linear slope distributes lens echoes in time, which smear or reduce formation of a constructive signals formed by the lens echoes. Additionally, the non-uniform thickness of the front layer decouples or detaches at least a portion of the lens reflections from the imaging plane to a reflection plane.

FIG. 1 is a schematic diagram of a diagnostic medical imaging system, specifically, an ultrasound imaging system 100. The ultrasound imaging system 100 includes an ultrasound probe 126 having a transmitter 122 and probe/SAP electronics 110. The ultrasound probe 126 may be configured to acquire ultrasound data or information from a region of interest (e.g., organ, blood vessel, heart) of the patient. The ultrasound probe 126 is communicatively coupled to the controller circuit 136 via the transmitter 122. The transmitter 122 transmits a signal to a transmit beamformer 121 based on acquisition settings received by the user. The signal transmitted by the transmitter 122 in turn drives the transducer elements 124 within the transducer array 112. The transducer elements 124 emit pulsed ultrasonic signals into a patient (e.g., a body). A variety of a geometries and configurations may be used for the array 112. Further, the array 112 of transducer elements 124 may be provided as part of, for example, different types of ultrasound probes.

The acquisition settings may define an amplitude, pulse width, frequency, and/or the like of the ultrasonic pulses emitted by the transducer elements 124. The acquisition settings may be adjusted by the user by selecting a gain setting, power, time gain compensation (TGC), resolution, and/or the like from the user interface 142.

The transducer elements 124 emit pulsed ultrasonic signals into a body (e.g., patient) or volume corresponding to the acquisition settings along one or more scan planes. The ultrasonic signals may include, for example, one or more reference pulses, one or more pushing pulses (e.g., shear-waves), and/or one or more pulsed wave Doppler pulses. At least a portion of the pulsed ultrasonic signals back-scatter from a region of interest (ROI) (e.g., heart, left ventricular outflow tract, breast tissues, liver tissues, cardiac tissues, prostate tissues, and the like) to produce echoes. The echoes are delayed in time and/or frequency according to a depth or movement, and are received by the transducer elements 124 within the transducer array 112. The ultrasonic signals may be used for imaging, for generating and/or tracking shear-waves, for measuring changes in position or velocity within the ROI (e.g., flow velocity, movement of blood cells), differences in compression displacement of the tissue (e.g., strain), and/or for therapy, among other uses. For example, the probe 126 may deliver low energy pulses during imaging and tracking, medium to high energy pulses to generate shear-waves, and high energy pulses during therapy.

The transducer array 112 may have a variety of array geometries and configurations for the transducer elements 124 which may be provided as part of, for example, different types of ultrasound probes 126. The probe/SAP electronics 110 may be used to control the switching of the transducer elements 124. The probe/SAP electronics 110 may also be used to group the transducer elements 124 into one or more sub-apertures.

The transducer elements 124 convert the received echo signals into electrical signals which may be received by a receiver 128. The receiver 128 may include one or more amplifiers, an analog to digital converter (ADC), and/or the like. The receiver 128 may be configured to amplify the received echo signals after proper gain compensation and convert these received analog signals from each transducer element 124 to digitized signals sampled uniformly in time. The digitized signals representing the received echoes are stored on memory 140, temporarily. The digitized signals correspond to the backscattered waves receives by each transducer element 124 at various times. After digitization, the signals still may preserve the amplitude, frequency, phase information of the backscatter waves.

Optionally, the controller circuit 136 may retrieve the digitized signals stored in the memory 140 to prepare for the beamformer processor 130. For example, the controller circuit 136 may convert the digitized signals to baseband signals or compressing the digitized signals.

The beamformer processor 130 may include one or more processors. Optionally, the beamformer processor 130 may include a central controller circuit (CPU), one or more microprocessors, or any other electronic component capable of processing inputted data according to specific logical instructions. Additionally or alternatively, the beamformer processor 130 may execute instructions stored on a tangible and non-transitory computer readable medium (e.g., the memory 140) for beamforming calculations using any suitable beamforming method such as adaptive beamforming, synthetic transmit focus, aberration correction, synthetic aperture, clutter reduction and/or adaptive noise control, and/or the like.

The beamformer processor 130 may further perform filtering and decimation, such that only the digitized signals corresponding to relevant signal bandwidth is used, prior to beamforming of the digitized data. For example, the beamformer processor 130 may form packets of the digitized data based on scanning parameters corresponding to focal zones, expanding aperture, imaging mode (B-mode, color flow), and/or the like. The scanning parameters may define channels and time slots of the digitized data that may be beamformed, with the remaining channels or time slots of digitized data that may not be communicated for processing (e.g., discarded).

The beamformer processor 130 performs beamforming on the digitized signals and outputs a radio frequency (RF) signal. The RF signal is then provided to an RF processor 132 that processes the RF signal. The RF processor 132 may generate different ultrasound image data types, e.g. B-mode, color Doppler (velocity/power/variance), tissue Doppler (velocity), and Doppler energy, for multiple scan planes or different scanning patterns. For example, the RF processor 132 may generate tissue Doppler data for multi-scan planes. The RF processor 132 gathers the information (e.g. I/Q, B-mode, color Doppler, tissue Doppler, and Doppler energy information) related to multiple data slices and stores the data information, which may include time stamp and orientation/rotation information, in the memory 140.

Alternatively, the RF processor 132 may include a complex demodulator (not shown) that demodulates the RF signal to form IQ data pairs representative of the echo signals. The RF or IQ signal data may then be provided directly to the memory 140 for storage (e.g., temporary storage). Optionally, the output of the beamformer processor 130 may be passed directly to the controller circuit 136.

The controller circuit 136 may be configured to process the acquired ultrasound data (e.g., RF signal data or IQ data pairs) and prepare frames of ultrasound image data for display on the display 138. The controller circuit 136 may include one or more processors. Optionally, the controller circuit 136 may include a central controller circuit (CPU), one or more microprocessors, a graphics controller circuit (GPU), or any other electronic component capable of processing inputted data according to specific logical instructions. Having the controller circuit 136 that includes a GPU may be advantageous for computation-intensive operations, such as volume-rendering. Additionally or alternatively, the controller circuit 136 may execute instructions stored on a tangible and non-transitory computer readable medium (e.g., the memory 140).

The controller circuit 136 is configured to perform one or more processing operations according to a plurality of selectable ultrasound modalities on the acquired ultrasound data, adjust or define the ultrasonic pulses emitted from the transducer elements 124, adjust one or more image display settings of components (e.g., ultrasound images, interface components, positioning regions of interest) displayed on the display 138, and other operations as described herein. Acquired ultrasound data may be processed in real-time by the controller circuit 136 during a scanning or therapy session as the echo signals are received. Additionally or alternatively, the ultrasound data may be stored temporarily in the memory 140 during a scanning session and processed in less than real-time in a live or off-line operation.

The memory 140 may be used for storing processed frames of acquired ultrasound data that are not scheduled to be displayed immediately or to store post-processed images (e.g., shear-wave images, strain images), firmware or software corresponding to, for example, a graphical user interface, one or more default image display settings, programmed instructions (e.g., for the controller circuit 136, the beamformer processor 130, the RF processor 132), and/or the like. The memory 140 may be a tangible and non-transitory computer readable medium such as flash memory, RAM, ROM, EEPROM, and/or the like.

The memory 140 may store 3D ultrasound image data sets of the ultrasound data, where such 3D ultrasound image data sets are accessed to present 2D and 3D images. For example, a 3D ultrasound image data set may be mapped into the corresponding memory 140, as well as one or more reference planes. The processing of the ultrasound data, including the ultrasound image data sets, may be based in part on user inputs, for example, user selections received at the user interface 142.

The controller circuit 136 is operably coupled to a display 138 and a user interface 142. The display 138 may include one or more liquid crystal displays (e.g., light emitting diode (LED) backlight), organic light emitting diode (OLED) displays, plasma displays, CRT displays, and/or the like. The display 138 may display patient information, ultrasound images and/or videos, components of a display interface, one or more 2D, 3D, or 4D ultrasound image data sets from ultrasound data stored in the memory 140 or currently being acquired, measurements, diagnosis, treatment information, and/or the like received by the display 138 from the controller circuit 136.

The user interface 142 controls operations of the controller circuit 136 and is configured to receive inputs from the user. The user interface 142 may include a keyboard, a mouse, a touchpad, one or more physical buttons, and/or the like. Optionally, the display 138 may be a touch screen display, which includes at least a portion of the user interface 142.

For example, a portion of the user interface 142 may correspond to a graphical user interface (GUI) generated by the controller circuit 136 shown on the display. The GUI may include one or more interface components that may be selected, manipulated, and/or activated by the user operating the user interface 142 (e.g., touch screen, keyboard, mouse). The interface components may be presented in varying shapes and colors, such as a graphical or selectable icon, a slide bar, a cursor, and/or the like. Optionally, one or more interface components may include text or symbols, such as a drop-down menu, a toolbar, a menu bar, a title bar, a window (e.g., a pop-up window) and/or the like. Additionally or alternatively, one or more interface components may indicate areas within the GUI for entering or editing information (e.g., patient information, user information, diagnostic information), such as a text box, a text field, and/or the like.

In various embodiments, the interface components may perform various functions when selected, such as measurement functions, editing functions, database access/search functions, diagnostic functions, controlling acquisition settings, and/or system settings for the ultrasound imaging system 100 performed by the controller circuit 136.

Figure 2:
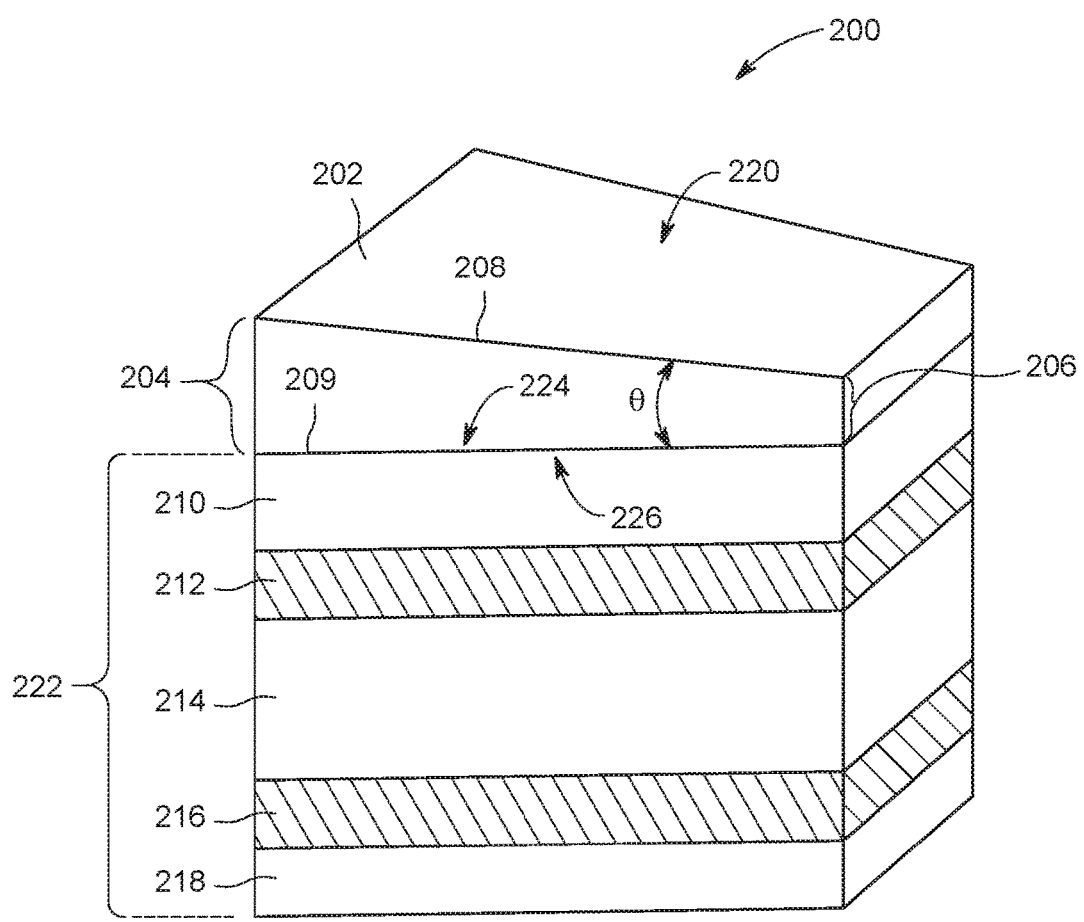
FIG. 2 illustrate a transducer element of an ultrasound probe, in accordance with an embodiment.

FIG. 2 illustrates a transducer element 200 of an ultrasound probe, in accordance with an embodiment. For example, the transducer element 200 may be similar to and/or the same as one of the transducer elements 124 of the transducer array 112 shown in FIG. 1. Each of the transducer elements 200 generate ultrasound signals (e.g., acoustic waves) that are directed toward a target, such as the ROI. At least a portion of the ultrasound signals are reflected off the target back toward the transducer element 200 as echoes.

The transducer element 200 may include a housing (not shown) that provides structural support for the transducer element 200. For example, the housing may be an enclosure that forms a body of the ultrasound probe 126 (shown in FIG. 1). The transducer element 200 may include a front layer 202 mounted to an acoustic stack 222. The acoustic stack 222 may include a piezoelectric layer 214 formed from a piezoelectric material (e.g., piezoelectric crystals), or a material that generates an electric charge in response to an applied mechanical force and that generates a mechanical force in response to an applied electric charge. The piezoelectric material may be, for example, lead zirconate titanate (PZT). Alternatively, other piezoelectric materials may be used. While the illustrated transducer element 200 includes only a single piezoelectric layer 214, alternatively a plurality of piezoelectric layers 214 may be provided. For example, the transducer element 200 may include two or more piezoelectric layers 214 stacked on each other.

The piezoelectric layer 214 may be coupled to a ground electrode 212 and a signal electrode 216. The electrodes 212, 216 are electrically conductive bodies, such as layers that include or are formed from one or more metals or metal alloys. The electrodes 212, 216 may be provided as layers that extend over all or substantially all of the footprint of the piezoelectric layer 214, or may be provided as another shape and/or extend over less than all of the footprint of the piezoelectric layer 214. The electrodes 212, 216 may be conductively coupled to probe/SAP electronics, such as the probe/SAP electronics 110 by one or more busses, wires, cables, and the like. For example, the probe/SAP electronics 110 control transmission and reception of electronic signals to and from the signal electrode 216. The ground electrode 212 may be conductively coupled to an electric ground reference of the probe/SAP electronics. The ground electrode 212 may convey at least some electric charge generated by the piezoelectric layer 214 to the electric ground reference to avoid interference or crosstalk with the electric charge conveyed to the signal electrode 216.

In a transmission mode of the probe/SAP electronics, the signal electrode 216 may receive transmit pulse signals that apply a charge to the signal electrode 216. The applied charge causes the piezoelectric layer 214 to emit ultrasound signals (e.g., acoustic waves) in one or more directions. When the piezoelectric layer 214 receives an acoustic echo, the received acoustic echo may cause mechanical strain in the piezoelectric layer 214, which creates an electric charge in the piezoelectric layer 214. The electric charge is conducted to the signal electrode 216, which conveys the electric charge to the probe/SAP electronics.

The acoustic stack 222 may also include one or more matching layers 210 and a front layer 202 or lens. The matching layers 210 are disposed between the front layer 202 and the piezoelectric layer 214. For example, the matching layers 210 may be coupled to the front layer 202 and the piezoelectric layer 214 on opposing sides of the matching layers 210. The matching layers 210 further have acoustic impedance characteristics between the acoustic impedance characteristics of the piezoelectric layer 214 and the front layer 202. For example, the font face 202 may have a relatively low acoustic impedance characteristic while the piezoelectric layer 214 has a relatively large acoustic impedance characteristic. The matching layers 210 may have one or more acoustic impedance characteristics that are greater than the acoustic impedance characteristic of the front layer 202 and less than the acoustic impedance characteristic of the piezoelectric layer 214. The intermediate acoustic impedance characteristic(s) of the matching layers 210 can reduce the difference between the acoustic impedance characteristics of the front layer 202 and the piezoelectric layer 214. The matching layers 210 can provide a transition region where the mismatch is gradually reduced in order to decrease the reflected acoustic waves.

A backing layer assembly 218 may be disposed below the piezoelectric layer 214. For example, the backing layer assembly 218 may be separated from the piezoelectric layer 214 by the signal electrode 216. Alternatively, the backing layer assembly 218 may at least partially abut the piezoelectric layer 214. The backing layer assembly 126 includes a thermally conductive body (not shown) held within a matrix enclosure. The thermally conductive body may include, or is formed from, one or more materials that conduct thermal energy or heat more than the matrix enclosure. For example, the thermally conductive body may conduct thermal energy away from the piezoelectric layer 214 and other components in the housing (such as other electronic components in a probe head that includes the transducer element 200 and is manipulated by an operator to image a body). In one embodiment, the backing layer assembly 218 may include one or more additional de-matching layers (not shown) disposed between the piezoelectric layer 214 and the thermally conductive body. The de-matching layers can abut the piezoelectric layer 214. The de-matching layers may be relatively thin layers (e.g., less than one wavelength of the acoustic pulses generated by the piezoelectric layer 214). The de-matching layers can have relatively high acoustic impedance characteristics such that the de-matching layers absorb or otherwise reduce the amount or energy of the acoustic pulses that are directed out of the piezoelectric layer 214 toward the thermally conductive body.

In the illustrated embodiment, the front layer 202 is a body having a transmission surface 220 through which the ultrasound signals generated by the piezoelectric layer 214 are emitted. The transmission surface 220 may be a patient engaging surface. For example, the transmission surface 220 may be positioned adjacent or in contact with the patient or the ROI during a scan of an ultrasound imaging system, such as the ultrasound imaging system 100. The front layer 202 is mounted to the acoustic stack 222. For example, the front layer 202 includes a mounting face 226 extending along an exterior surface of the base 209. The acoustic stack 222 may include a front mounting face 224 extending along an exterior surface of the matching layers 210. The front layer 202 may be mounted to the acoustic stack 222 by positioning the mounting face 226 onto the front mounting face 224 and aligning the acoustic stack with the front layer 202. For example, mounting the front layer 202 to the acoustic stack 222 allows the opposing edges 204 and 206 to extend from the acoustic stack 222.

The front layer 202 may be formed from a material having a relatively low acoustic impedance characteristic relative to the piezoelectric layer 214. An acoustic impedance characteristic represents the resistance of a material to the passage of an acoustic wave through the material. For example, the front layer 202 may be formed from a silicone rubber. Alternatively or alternatively, the front layer 202 may be formed from another material.

The front layer 202 includes two opposing edges 204 and 206. The opposing edges 204, 206 have different heights that form a slope or incline 208 of the transmission surface 220 of the front layer 202. It may be noted that the incline may be linear. As shown in FIG. 2, the height of the edge 204 is greater than the height of the edge 206. For example, the edge 204 may have a height of approximately 1.5 millimeters and the edge 206 may have a height of approximately 0.5 mm. The slope or incline 208 forms an angle $\theta$ with respect to a base 209 of the front layer 202. Additionally, the slope or incline 208 and base 209 of the front layer 202 provides or forms the wedge shape of the front layer 202, which extends from the opposing edge 206 to the opposing edge 204 at the angle $\theta$. In various embodiments, the angle $\theta$ may be approximately three to five degrees. It may be noted that in other embodiments the angle $\theta$ may be less than three degrees or more than five degrees.

The transmission surface 220 extends along the incline 208. Based on the slope or incline 208, the transmission surface 220 of the front layer 202 may correspond to an angled plane. For example, the transmission surface 220 extends a long a plane oriented at an angle with respect to the mounting face 226 of the base 209 or the front mounting face 224 of the acoustic stack 222, which adjusts a direction (e.g., by refraction) of the ultrasound signals generated by the piezoelectric layer 214.

In operation, the transducer element 200 may be combined with a plurality of other transducer elements 200, for example, to form a transducer array 300 as shown in FIG. 3A. The transducer array 300 may be similar to and/or the same as the transducer array 112 shown in FIG. 1. FIG. 3B illustrates a cross section of the transducer array 300. For example, the cross section may correspond to a row or set of transducer elements 350 of the transducer array 300 extending along an axis 310 and normal or perpendicular to an axis 312. The transducer array 300 includes a front layer 302 extending along a surface of the acoustic stacks 222 of the plurality of transducer elements 200. The front layer 302 includes a base and a transmission surface 320 terminating at opposing edges 304 and 306 of the front layer 302. The front layer 302 is formed by an arrangement and/or relative positions of the plurality of transducer elements 200 forming the transducer array 300. For example, as shown in FIG. 3B, the inclines 208a-d of the transducer elements 200a-d each may have the same and/or identical slope. The transducer elements 200a-d are positioned such that the inclines 208a-d successively from a continuous incline 308. Optionally, the incline 308 may be a linear incline forming a wedge shape of the front layer 302 terminating at the opposing edges 304 and 306. The incline 308 is defined by the arrangement and slope inclines 208 of the transducer elements 200 forming the transducer array 300. For example, the opposing edges 304 and 306 may have different lengths that form the incline 308. Additionally, one or more planes of the transmission surface 320 is based on the incline 308 of the front layer 302.

In various embodiments, the front layer 302 of the transducer array 300 may have other polygonal shapes other than the wedge shape shown in FIG. 3B. For example, in reference to FIG. 4, the plurality of transducer elements 200 forming a transducer array may be positioned relative to each other to have a transmission surface with multiple planes.

Figure 4:
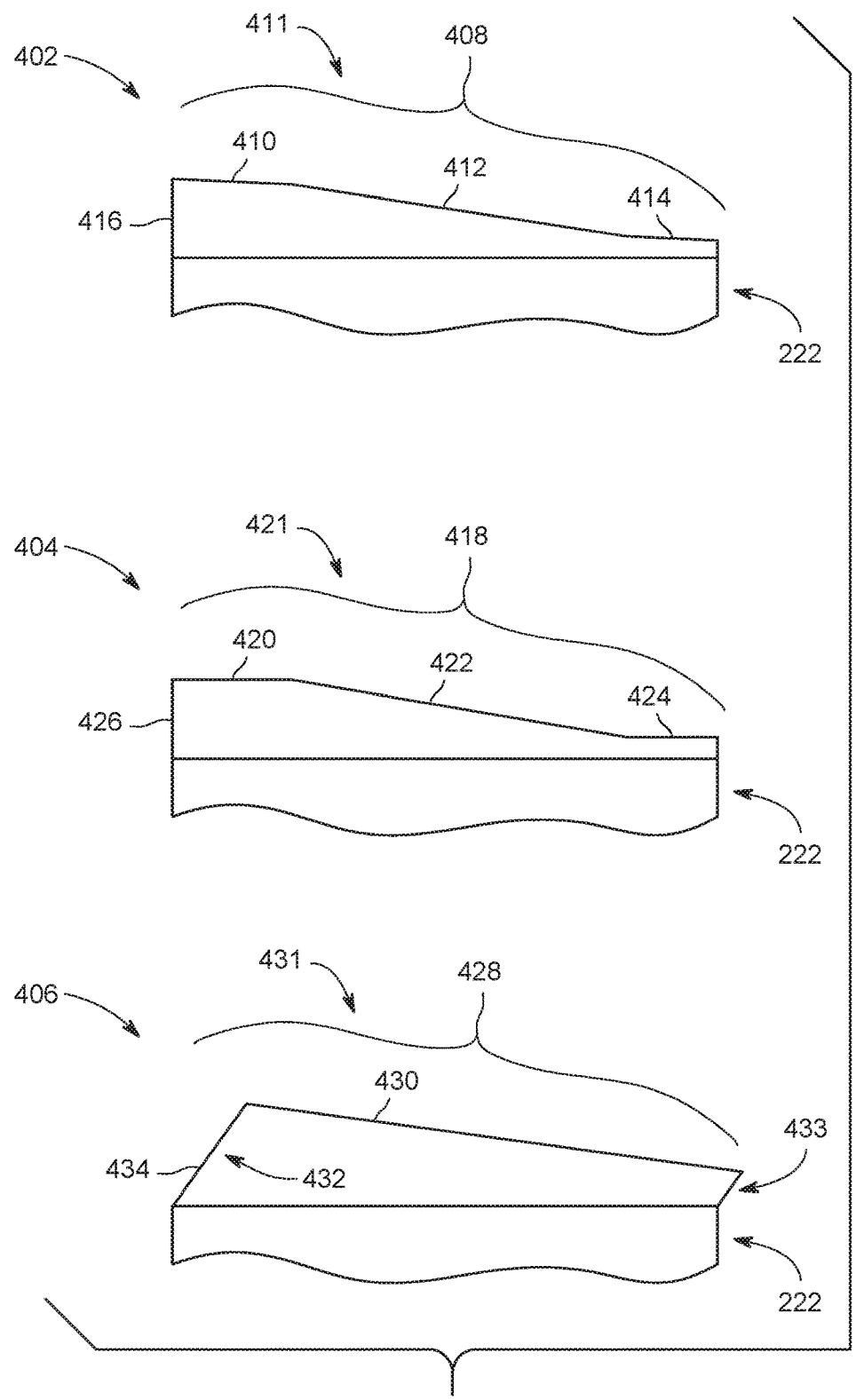
FIG. 4 illustrates cross sections of a transducer array, in accordance with various embodiments.

FIG. 4 illustrates cross sections 402-406 of a transducer array, in accordance with various embodiments. For example, the cross sections 402-406 may correspond to a row or set of transducer elements of an alternative embodiments of the transducer array 300 extending along the axis 310 and normal or perpendicular to the axis 312. Each of the cross sections 402-406 have a front layer 416, 426, 434 configured as a polygonal shape, but are not a wedge shape. For example, the cross section 402 includes an incline 408 that is nonlinear. The incline 408 is formed by a first set of transducer elements 200 having first inclines 410, 414 and a second set of transducer elements 200 having a second incline 412. The second incline 412 is shown having a larger slope magnitude relative to slope magnitudes of the first inclines 410, 414. The arrangement and difference in slope magnitudes of the inclines 410-414 produce the nonlinear incline 408. For example, the second set of transducer elements 200 are interposed between the first set of transducer elements 200. It may be noted, a transmission surface 411 of the front layer 416 includes multiple angled planes based on the first inclines 410, 414 and the second inclined 412.

Additionally or alternatively, the transducer array may include an incline 418 having a slope extending at least a portion of the transducer array 300. For example, the incline 418 of the cross section 404 is formed by a first set of transducer elements 200 having an incline 422 interposed with a second set of transducer elements 200 having orthogonal and/or approximately orthogonal segments 420, 424. The transducer array may be configured to have more first set of transducer elements 200 relative to the second set of transducer elements, such as the slope by the incline 422 extends a large portion of the transducer array. For example, the transducer array may be configured to have a greater portion of the transmission surface 421 along an angle plane defined by the incline 422 relative to the segments 420, 424.

Optionally, the transducer array may include a front layer 432 having a shifted transmission surface 431 with respect to the acoustic stack 222. For example, opposing edges 433-434 of the front layer 423 may extend from the acoustic stacks 222 at an angle forming an incline 428 of the transmission surface 431.

Referring to FIG. 3B, the transmission surface 320 extends along the incline 308. Based on the slope or incline 308, the transmission surface 320 of the front layer 302 may a direction (e.g., by refraction) of the ultrasound signals generated by the piezoelectric layer 214. For example, in connection with FIG. 5, the transmission surface 320 adjusts a trajectory or direction of the ultrasound signals 504 at the transmission surface 320 based on the plane of the transmission surface 320

Figure 5:
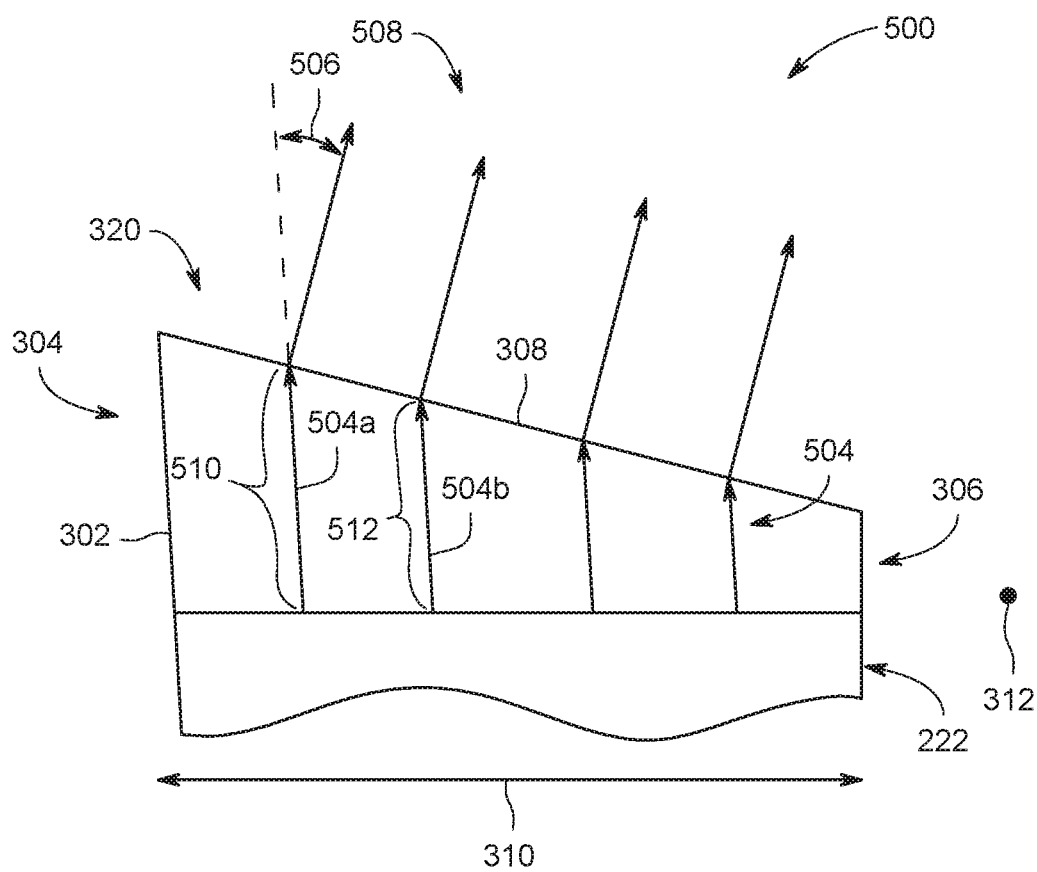
FIG. 5 illustrates ultrasound signals emitted from the transducer array viewed along a cross section, in accordance with an embodiment.

FIG. 5 illustrates ultrasound signals 504 emitted from the transducer array 300 viewed along a cross section 500, in accordance with an embodiment. For example, the cross section 500 may correspond to the set of transducer elements 350 shown in FIG. 3B along the axis 310 and normal or perpendicular to the axis 312. The ultrasound signals 504 may be generated by the acoustic stack 222 of the plurality of transducer elements 200 forming the transducer array 300 and received by the front layer 302. The ultrasound signals 504 traverse through the front layer 302 and are emitted from the transmission surface 320 as ultrasound signals 508. The ultrasound signals 508 may form an imaging plane of the ultrasound probe 126 that is perpendicular to a trajectory or direction of the ultrasound signals 508. As shown in FIG. 5, the ultrasound signals 508 are emitted at a trajectory or direction normal or approximately normal with respect to the angled plane of the transmission surface 320. In various embodiments, the ultrasound signals 508 may be within fifteen degrees of the normal angle of the transmission surface 320. For example, the trajectory of the ultrasound signals 504 within the front layer 302 is refracted by an angle 506 to form the ultrasound signals 508. The refracted angle 506 may be based on an angle θ of the transmission surface 320 and a ratio of the refraction index or index of refraction of the front layer 302 ($n_1$) and the patient ($n_2$). For example, the refracted angle 506 ($\theta_2$) may be calculated based on Equation 1 shown below.

$$\theta_2 = \sin^{-1}\left(\frac{n_1}{n_2} \cdot \sin\theta\right)$$ Equation (1)

Additionally or alternatively, when the incline 308 of the front layer 302 corresponds to a linear incline the trajectories or route of the ultrasound signals 508 are parallel with respect to each other. The incline 308 defines the angled plane of the transmission surface 320. The angled plane is a uniform or even surface of the transmission surface 320, which uniformly adjust a direction of the ultrasound signals 504 based on an angle of the angled plane. For example, normal angles along the transmission surface 320 are alike and parallel relative to each other. Based on the uniform or even surface of the transmission surface 320 each of the normal angles along the transmission surface 320 may be approximately the same. The uniform surface of the transmission surface 320 enables each of the ultrasound signals 508 to have a trajectory or path emitted from the transmission surface 320 to be aligned with each other. For example, the ultrasound signals 508 may not intersect or cross each other.

In operation, a portion of the ultrasound signals 504 within the front layer 302 are reflected based on an acoustic impedance of the front layer 302. For example, approximately one to three percent of the ultrasound signals 504 may not be emitted by the transmission surface 320, and are reflected back into the front layer 302. In connection with FIGS. 6 and 7, the reflected ultrasound signals 608 may be emitted by the transmission surface 320 and temporally separated or spatially spread apart with respect to each other.

Figure 6:
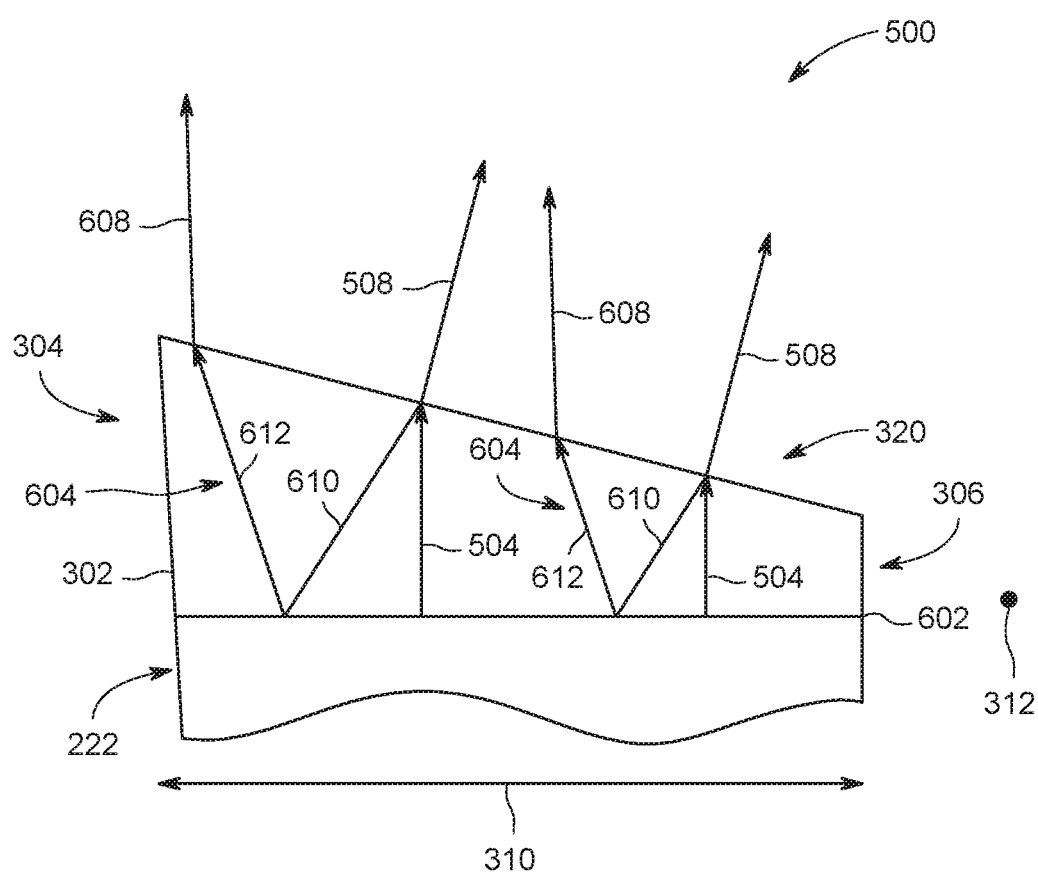
FIG. 6 illustrates ultrasound double pinning based on ultrasound signals emitted by the transducer array, in accordance with an embodiment.

FIG. 6 illustrates ultrasound double pinning based on the ultrasound signals 504, in accordance with an embodiment. The ultrasound double pinning corresponds to lens echoes represented by the reflected ultrasound signals 608 emitted from the transmission surface 320. For example, a portion of the ultrasound signals 504 are reflected at the transmission surface 320 and back into the front layer 302 forming reflected ultrasound signals 604. It may be noted that the reflected ultrasound signals 608 are not in parallel to the ultrasound signals 508.

Additionally or alternatively, the front layer 302 is configured to spatially separate the reflected ultrasound signals 608 generated from the ultrasound signals 508 in contact with the transmission surface 320. For example, the reflected ultrasound signals 604 may be subdivided into two segments 610, 612 that traverse in two opposing directions prior to being emitted at the transmission surface 320 as the reflected ultrasound signals 608. The first segment 610 of the reflected ultrasound signals 604 traverse in an opposing direction with respect to the ultrasound signal 504 towards a base of the front layer 302. The base may corresponding to a boundary 602 representing a mirror plane separating the front layer 302 and the acoustic stacks 222 of the transducer elements 200 forming the transducer array 300. The first segment 610 of the ultrasound signals 604 meets the boundary 602 at an incident angle with respect to the mirror plane and/or base of the front layer 302. At least a portion of the reflected ultrasound signals 604 along the first segment 610 is deflected at the boundary 602 to form the second segment 612. The second segment 612 of the reflected ultrasound signals 604 extends along a second direction towards the transmission surface 320. The second segment 612 of the ultrasound signals 604 is aligned along an angle with respect to the mirror plane and/or base of the front layer 302 towards the transmission surface 320. The angle being defined by the incident angle of the first segment 610 and the plane of the boundary 602. As shown in FIG. 6, a trajectory of the second segment 612 of the reflected ultrasound signals 604 is different with respect to the ultrasound signals 504. Similarly to forming the ultrasound signals 508, the trajectory of the second segment 612 of the reflected ultrasound signals 604 within the front layer 302 are refracted based on the plane of the transmission surface 220, to form the reflected ultrasound signals 608 emitted at the transmission surface 220.

It may be noted that the second segment 612 meets the transmission surface 320 at a different incident angle relative to the ultrasound signals 504. The different incident angles of the second segment 612 relative to the ultrasound signals 504 produce different trajectories of the reflected ultrasound signals 608 relative to the ultrasound signals 508. The different trajectories spatially separate the reflected ultrasound signals 608 with respect to the ultrasound signals 508. For example, the imaging plane formed by the ultrasound signals 508 are separated in space from a plane formed by the reflected ultrasound signals 608.

Figure 7:
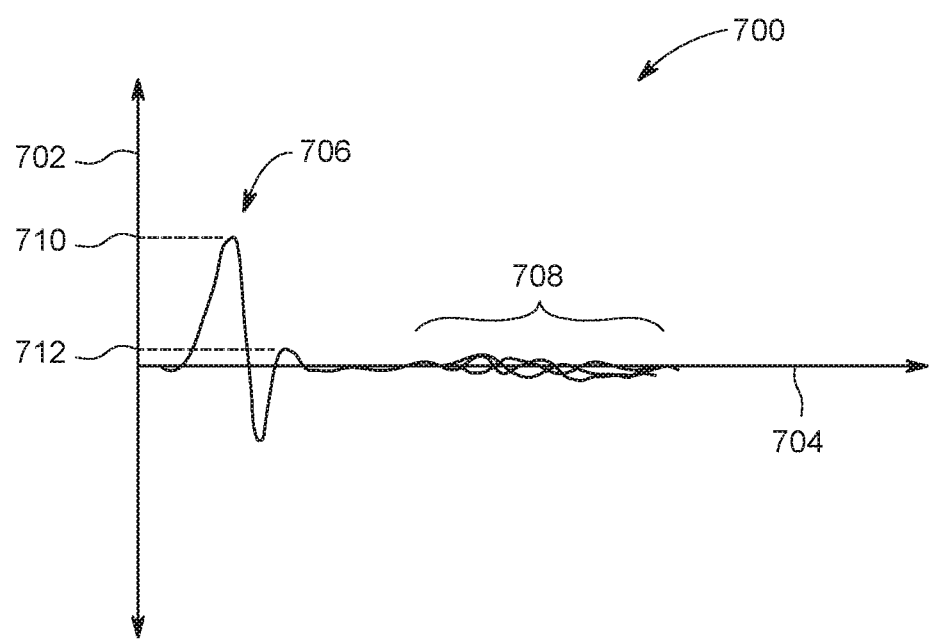
FIG. 7 is a graphical representation of ultrasound signals transmitted by the transducer array of FIG. 5, in accordance with an embodiment.

FIG. 7 is a graphical representation 700 of ultrasound signals 604-608 transmitted by the transducer array 300, in accordance with an embodiment. The graphical representation 700 is plotted along a horizontal axis 704 representing time and a vertical axis 702 representing amplitude of the ultrasound signals 508, 608. The ultrasound signals 508 are shown as an acoustic wave 706, and the ultrasound signals 608 are shown as a series of acoustic waves 708. The series of acoustic waves 708 are illustrated temporally separated from the acoustic wave 706.

The acoustic wave 706 may be formed by the superposition of the ultrasound signals 508 emitted by the transmission surface 320 of the transducer array 300. For example, the ultrasound signals 508 may be configured to be temporally aligned with each other by a transmit beamformer (e.g., the transmit beamformer 121 shown in FIG. 1) operatively coupled to the acoustic stacks 322 of the transducer elements 200 forming the transducer array 300. By temporally aligning the ultrasound signals 508, each of the ultrasound signals are concurrently and/or simultaneously emitted from the transmission surface 320. For example, each of the ultrasound signals 508 may be incident at the same point when emitted from the transmission surface 320, which allows for constructive interference or superposition of the ultrasound signals 508 to form the acoustic wave 706. The superposition of the ultrasound signals 508 allow each ultrasound signal 508 to sum together forming the acoustic wave 706.

In various embodiments, to temporally align the ultrasound signals 508 portions of the ultrasound signals 504 may be temporally delayed based on a shape of the front layer 302. For example, the transmit beamformer may instruct the acoustic stacks 222 to delay one or more of the ultrasound signals 504 based on the relative position of the ultrasound signals 504 within the front layer 302. Optionally, the transmit beamformer may time delay each of the ultrasound signals 504 at differently.

Returning to FIG. 5, the ultrasound signal 504a and the ultrasound signal 504b traverse along different paths within the front layer 302. For example, the ultrasound signal 504a and the ultrasound signal 504b traverse a distance 510 and 512, respectively, to intersect or reach the transmission surface 320. The distances 510, 512 are different based on the position of the ultrasound signals 504a-b relative to the front layer 302. For example, the distances traversed by the ultrasound signals 504 proximate to the edge 304 are longer relative to the distances traversed by the ultrasound signals 504 proximate to the edge 306 from the base of the front layer 302 (e.g., the border 602 shown in FIG. 6) to the transmission surface 320. An amount of the temporal delay of each of the ultrasound signals 504 may be based on a position of the each of the ultrasound signals 504 with respect to the front layer 302, which corresponds to the distance traversed by the ultrasound signals 504 within the front layer 302. For example, since the distance 512 to be traversed by the ultrasound signal 504b is shorter than the distance 510 to be traversed by the ultrasound signal 504a, the ultrasound signal 504b may be temporally delayed (e.g., subsequent to) relative to the ultrasound signals 504a. Thereby, the ultrasound signal 504a may be received by the front layer 302 prior to the ultrasound signal 504b, which allows the ultrasound signal 504a to temporally align with the ultrasound signal 504b when reaching or intersecting the transmission surface 420.

Alternatively, based on the shape of the front layer 302, the lens echoes corresponding to the ultrasound signals 608 (shown in FIG. 6) are temporally shifted with respect to each other. The temporal shift further reduces constructive interference of the reflected ultrasound signals 608 resulting in the series of acoustic waves 708 (FIG. 7). For example, each of the ultrasound signals 604 are reflected at the transmission surface 320 concurrently and/or simultaneously with each other toward the boundary 602 based on the temporal alignment of the ultrasound signals 504. As the ultrasound signals 604 traverse within the front layer 302, each of the ultrasound signals 604 may traverse a different distance based on the shape of the front layer 302. Based on the different distances traversed by the ultrasound signals 604 within the front layer 302, the ultrasound signals 604 are reflected at the boundary 602 at different times. For example, the ultrasound signals 604 proximate to the edge 306 may be reflected by the boundary 602 prior to the ultrasound signals 604 proximate to the edge 304, which creates a temporal shift between the ultrasound signals 604. Additionally, the ultrasound signals 604 intersect the transmission surface 320 at different times. For example, when the ultrasound signals 604 away from to the boundary 602 toward the transmission surface 320, the ultrasound signals 604 proximate to the edge 306 may intercept or reach the transmission surface 320 prior to the ultrasound signals 604 proximate to the edge 304. Thereby, the ultrasound signals 608 proximate to the edge 306 may be emitted by the transmission surface 320 prior to the ultrasound signals 608 proximate to the edge 304.

The temporal shift between the ultrasound signals 608 emitted by the transmission surface 320 based on a shape of the front layer 302 reduces the effect or formation of constructive interference by the ultrasound signals 608. For example, each of the ultrasound signals 608 are emitted by the transmission surface 320 at different times such that the ultrasound signals 608 may not be incident at the same point (e.g., phase shift with respect to each other) prohibiting and/or reducing the effect of constructive interference between the ultrasound signals 608. Based on the temporal shift of the ultrasound signals 608, a plurality of the ultrasound signals 608 may form acoustic waves, which corresponds to the series of acoustic waves 708 shown in FIG. 7.

Figure 8:
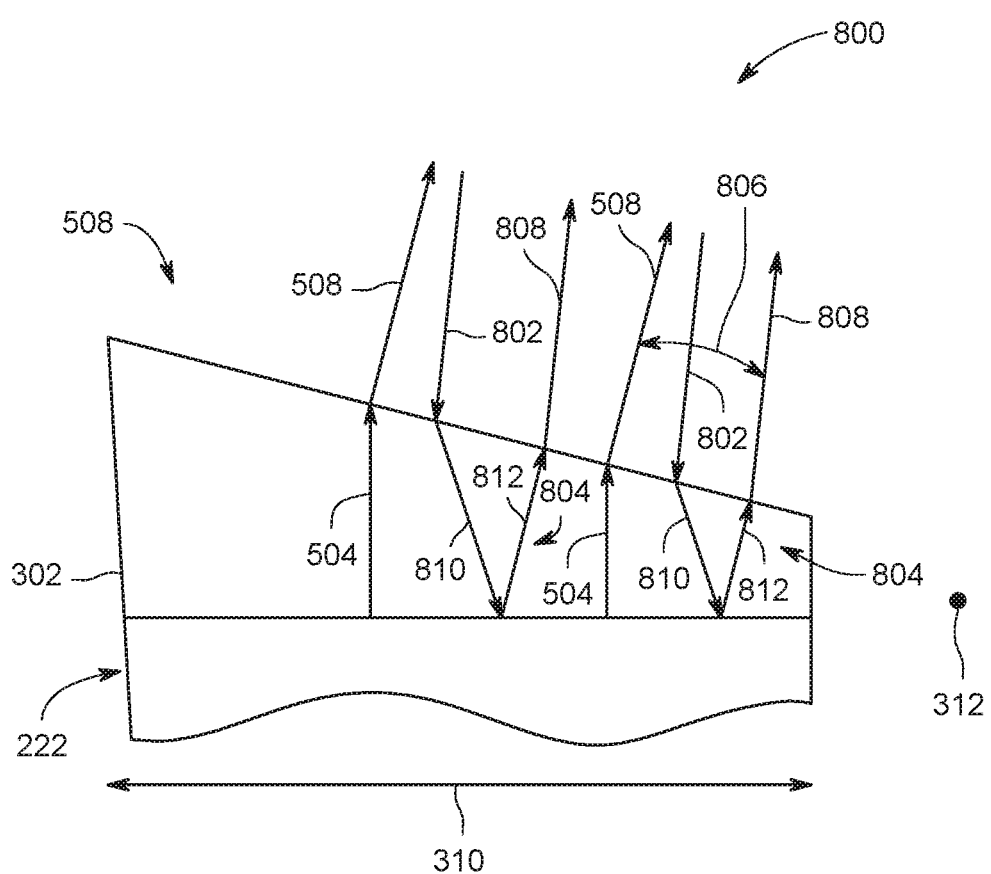
FIG. 8 illustrates reflected artifact signals emitted from the transducer array viewed along a cross section, in accordance with an embodiment.

FIG. 8 illustrates reflected artifact signals 808 emitted from the transducer array 300 viewed along a cross section 800. For example, the cross section 800 may be similar to and/or the same as the cross section 500 shown in FIG. 5. The reflected ultrasound signals 808 may be based on echoes from the ROI. For example, at least a portion of the ultrasound signals 508 are reflected from the ROI as reflected ultrasound signals 802 (e.g., echoes), which are received by the transmission surface 320. The transmission surface 320 refracts the reflected ultrasound signals 802 by adjusting a trajectory or direction of the reflected ultrasound signals 802 based on an incident angle of the reflected ultrasound signals 802 with respect to the transmission surface 320. For example, the refraction of the reflected ultrasound signals 802 at the transmission surface 320 may be based on an angle of the reflected ultrasound signals 802 with respect to the normal angle of the transmission surface 320 and a ratio of the refraction index of the patient and the front layer 302.

The result of the refraction of the reflected ultrasound signals 802 at the transmission surface 320 are the received ultrasound signals 804. It may be noted that the reflected ultrasound signals 802 may be in parallel or oblique (as shown in FIG. 8) with respect to the ultrasound signals 508 based on the ROI.

For example, as shown in FIG. 8, the reflected ultrasound signals 802 may not be in parallel to the ultrasound signals 508. The difference in alignment is due to an oblique reflection of the ultrasound signals 508 on the ROI. The received ultrasound signals 804 may be subdivided into two segments 810, 812 that traverse in two opposing directions prior to being emitted at the transmission surface 320 as the reflected artifact signals 808. The first segment 810 of the received ultrasound signals 804 traverse within the front layer 302 from the transmission surface 320 to the boundary 602. The first segment 810 meets the boundary 602 at an incident angle with respect to a mirror plane and/or base of the front layer 302. At least a portion of the received ultrasound signals 804 along the first segment 810 is reflected at the boundary 602 to form the second segment 812. The second segment 812 of the received ultrasound signals 804 extends along a direction back into the front layer 302. For example, the portion of the received ultrasound signals 804 is directed towards the transmission surface 320 aligned along an angle with respect to a mirror plane and/or base of the front layer 302. The angle being defined by the incident angle of the first segment 810 and the plane of the boundary 602.

The reflected artifact signals 808 are emitted by the transmission surface 320 with a different trajectory or direction relative to the received ultrasound signals 802. For example, the reflection of the received ultrasound signals 812 are refracted at the transmission surface 320 based on the angle of the transmission surface 320 and a ratio of the refraction index of the front layer 302 and the patient.

It may be noted that the trajectory or direction of the reflected artifact signals 808 are not parallel to the ultrasound signals 508 or the reflected ultrasound signals 802. The reflected artifact signals 808 are based on acoustic signals that pass through or cross the transmission surface 320 twice. For example, when the reflected ultrasound signals 802 cross the transmission surface 320 to form the received ultrasound signals 804, and when the received ultrasound signals 804 cross the transmission surface 320 to form the reflected artifact signals 808. The multiple refractions by the transmission surface 320 adjusts a trajectory or direction of the received ultrasound signals 804 differently than the ultrasound signals 504. For example, an angle of the ultrasound signals 504 relative to the transmission surface 320 is different than the angle of the received ultrasound signals 804 with respect to the boundary 602. The difference in angles off set the received ultrasound signals 804 relative to the ultrasound signals 504. For example, the refraction or change in trajectory of the received ultrasound signals 804 form the reflected artifact signals 808 offset by an angle 806 relative to the ultrasound signals 508.

Additionally or alternatively, the offset angle 606 of the reflected artifact signals 808 corresponds to a different imaging plane than the imaging plane formed by the ultrasound signals 508. For example, the imaging plane of the reflected artifact signals 808 are decoupled or detached from the imaging plane formed by the ultrasound signals 508 based on the offset angle 806. Based on the different imaging plane of the reflected artifact signals 808, the reflected artifact signals 808 are filtered by the probe/SAP electronics (e.g., the probe/SAP electronics 110) and/or the receiver (e.g., the receiver 128).

Figure 9:
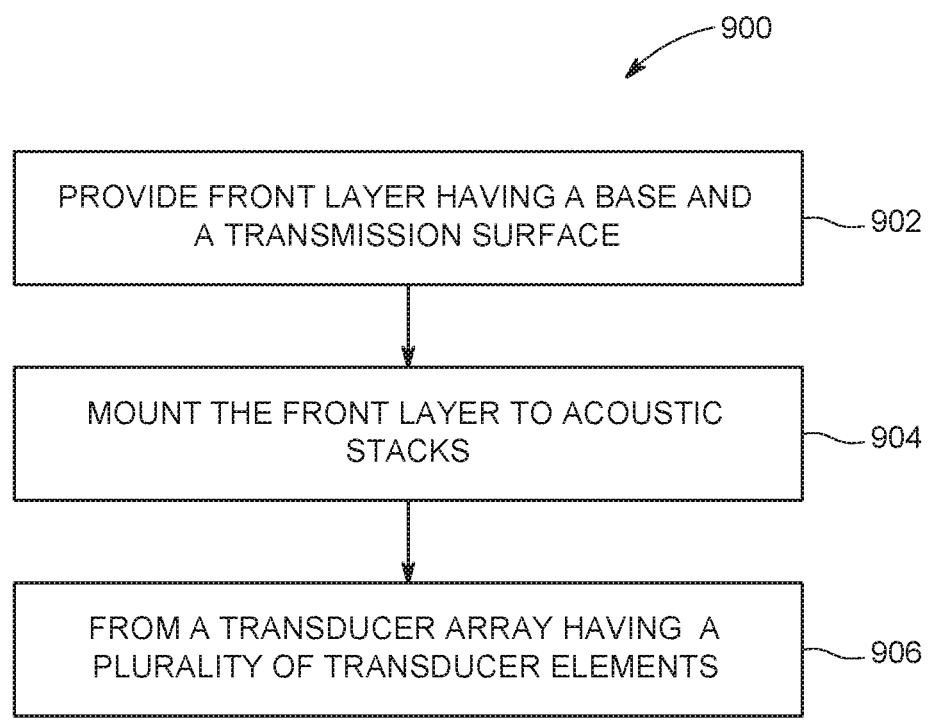
FIG. 9 illustrates a flow chart of a method in accordance with an embodiment.

FIG. 9 is a flow chart of a method 900 in accordance with an embodiment. The method 900 may be, for example, a method of manufacturing or assembling a transducer array with a front layer (e.g., the front layer 302). The method 900 may employ structures or aspects of various embodiments (e.g., systems and/or methods) discussed herein. In various embodiments, certain steps may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion.

The method 900 includes providing, at 902, a front layer that includes a base and a transmission surface The front layer may be similar to or the same as, for example, the front layer 302 (FIGS. 3-6). The front layer includes a transmission surface extending along the linear incline. For example, the transmission surface may extend along a plane oriented at an angle with respect to a mounting surface of the base.

The method 900 also include mounting, at 904, the front layer to a plurality of acoustic stacks. The acoustic stacks may be similar to or the same as, for example, the acoustic stack 222 of the transducer elements 200 (FIG. 2). For example, the front layer may include a mounting face. The mounting face may extend along an exterior surface are of the base, for example, an opposing surface area of the transmission surface 320. The acoustic stack may include a front mounting face. The front layer may be mounted to the acoustic stacks of the transducer elements by positioning the mounting face onto the front mounting face. For example, when mounted the mounting face is adjacent and in contact with the front mounting face. Additionally or alternatively, when mounted, the opposing edges of the front face may be aligned with at least two of the acoustic stacks. For example, the opposing edges may extend from the outer acoustic stacks or edges of the transducer array.

Figure 3:
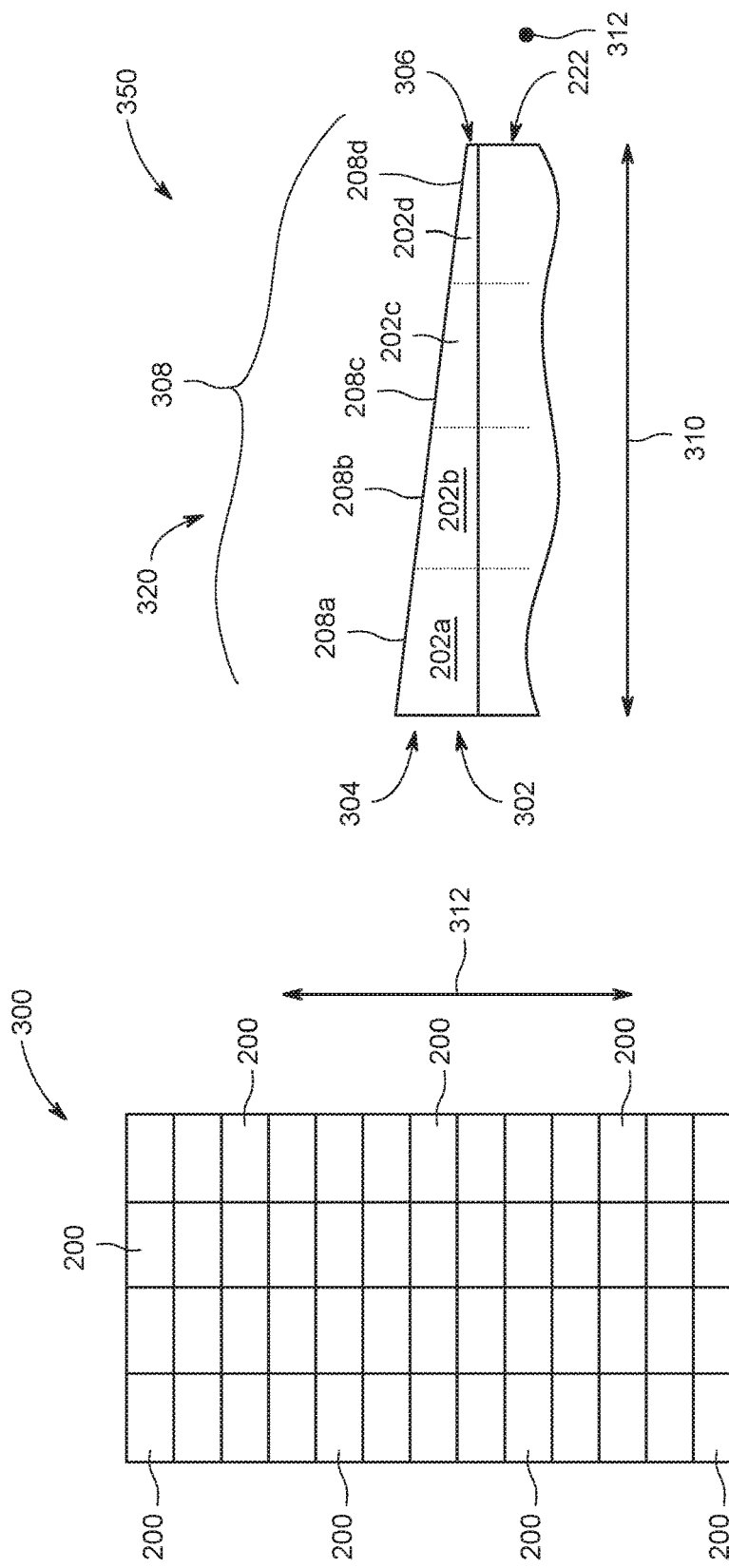
FIG. 3A illustrates a transducer array formed by a plurality transducer elements, in accordance with an embodiment.
FIG. 3B illustrates a cross section of the transducer array shown in FIG. 3A, in accordance with an embodiment.

The method 900 may also include forming a transducer array having a plurality of transducer elements at 906. The acoustic stack may be similar to or the same as, for example, the transducer array 300 (FIG. 3). Optionally, the transducer array may be enclosed in a housing. The housing may be an enclosure that forms a body of the ultrasound probe, such as the ultrasound probe 126. For example, the housing may enclose the acoustic stack of the transducer elements forming the transducer array and the opposing edges of the front layer. Additionally or alternatively, the housing may include a void or opening to expose the transmission surface of the transducer array. For example, the opening may allow the transmission surface to be in contact or adjacent with a patient or the ROI. The housing may be composed of plastic, ceramic, and/or the like.

It should be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid-state drive, optical disk drive, and the like. The storage device may also be other similar means for loading computer programs or other instructions into the computer or processor.

As used herein, the term "computer," "subsystem" or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein. Instead, the use of "configured to" as used herein denotes structural adaptations or characteristics, and denotes structural requirements of any structure, limitation, or element that is described as being "configured to" perform the task or operation. For example, a controller circuit, processor, or computer that is "configured to" perform a task or operation may be understood as being particularly structured to perform the task or operation (e.g., having one or more programs or instructions stored thereon or used in conjunction therewith tailored or intended to perform the task or operation, and/or having an arrangement of processing circuitry tailored or intended to perform the task or operation). For the purposes of clarity and the avoidance of doubt, a general purpose computer (which may become "configured to" perform the task or operation if appropriately programmed) is not "configured to" perform a task or operation unless or until specifically programmed or structurally modified to perform the task or operation.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f) unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal language of the claims.

What is claimed is:

1. A transducer array for an ultrasound probe comprising:
   a plurality of transducer elements arranged side by side in a row, each transducer element having an acoustic stack configured to generate ultrasound signals, wherein the acoustic stacks have respective front mounting faces that define a continuous line across the row; and
   a front layer having a height extending from a base surface of the front layer to a transmission surface of the front layer, wherein the front layer is mounted to the acoustic stacks of the plurality of transducer elements such that the base surface faces the acoustic stacks, the transmission surface includes a linear incline that is oriented transverse to the continuous line defined by the front mounting faces of the acoustic stacks, wherein the transmission surface is configured to emit the ultrasound signals.

2. The transducer array of claim 1, wherein at least a portion of the transmission surface extends along a plane oriented at an angle with respect to the base surface, the transmission surface configured to uniformly adjust a direction of the ultrasound signals based on the angle.

3. The transducer array of claim 1, wherein the front layer includes opposite first and second edges that each extend from the base surface to the transmission surface, the linear incline extending along the transmission surface and terminating at the opposite first and second edges, wherein the opposite first and second edges have different heights to form the linear incline.

4. The transducer array of claim 1, further comprising a transmit beamformer operatively coupled to the acoustic stacks, wherein the transmit beamformer is configured to time delay a first ultrasound signal with respect to a second ultrasound signal generated by the acoustic stacks, the time delay based on the relative positions of the first ultrasound signal and the second ultrasound signal within the front layer.

5. The transducer array of claim 1, wherein the transmission surface includes a second linear incline, wherein the second linear incline has a different slope with respect to the linear incline.

6. The transducer array of claim 1, wherein the front layer is configured to have reflected ultrasound signals emitted by the transmission surface at different times with respect to each other, wherein the reflected ultrasound signals are generated from the ultrasound signals in contact with the transmission surface.

7. The transducer array of claim 1, wherein the front layer is configured to spatially separate reflected ultrasound signals generated from the ultrasound signals in contact with the transmission surface.

8. The transducer array of claim 7, wherein a first reflected ultrasound signal is spatially separated from a second reflected ultrasound signal based on the relative positions of the first reflected ultrasound signal and the second reflected ultrasound signal within the front layer.

9. The transducer array of claim 1, wherein the ultrasound signals define an imaging plane, the front layer is configured to detach reflected artifact signals from the imaging plane, the reflected artifact signals are based on echoes generated in response to the ultrasound signals emitted by the transmission surface.

10. The transducer array of claim 1, wherein the linear incline forms a wedge shape of the front layer.

11. An ultrasound imaging system comprising:
    an ultrasound probe including a housing; and
    a transducer array enclosed within the housing, the transducer array formed by a plurality of transducer elements and a front layer, each transducer element having an acoustic stack configured to generate ultrasound signals, the front layer having a height extending from a base surface of the front layer to a transmission surface of the front layer, the transmission surface includes a linear incline that is oriented transverse to the base surface such that the front layer has a wedge shape,
    wherein the front layer is mounted to the acoustic stacks such that the base surface faces the acoustic stacks and the transmission surface is configured to emit the ultrasound signals from the transducer array.

12. The ultrasound imaging system of claim 11, wherein the transmission surface is configured to uniformly adjust a direction of the ultrasound signals based on the angle.

13. The ultrasound imaging system of claim 11, wherein the front layer includes opposite first and second edges that each extend from the base surface to the transmission surface, the linear incline extending along the transmission surface and terminating at the opposite first and second edges, wherein the opposite first and second edges have different heights to form the linear incline.

14. The ultrasound imaging system of claim 13, wherein the transmission surface is configured to refract the ultrasound signals such that ultrasound signals emitted by the transmission surface are in parallel with respect to each other.

15. The ultrasound imaging system of claim 11, further comprising a transmit beamformer operatively coupled to the acoustic stacks, wherein the transmit beamformer is configured to time delay a first ultrasound signal with respect to a second ultrasound signal generated by the acoustic stacks, the time delay based on the relative positions of the first ultrasound signal and the second ultrasound signal within the front layer.

16. The ultrasound imaging system of claim 11, wherein front layer is configured to have reflected ultrasound signals emitted by the transmission surface at different times with respect to each other, wherein the reflected ultrasound signals are generated from the ultrasound signals in contact with the transmission surface.

17. The ultrasound imaging system of claim 11, wherein the transmission surface includes a second linear incline, wherein the second linear incline has a different slope with respect to the linear incline.

18. The ultrasound imaging system of claim 11, wherein the front face is configured to spatially separate reflected ultrasound signals generated from the ultrasound signals in contact with the transmission surface.

19. The ultrasound imaging system of claim 18, wherein a first reflected ultrasound signal is spatially separated from a second reflected ultrasound signal based on the relative positions of the first reflected ultrasound signal and the second reflected ultrasound signal within the front layer.

20. A method for manufacturing a front layer for an ultrasound transducer array, the method comprising:
  providing a front layer, wherein the front layer has a height extending from a base surface of the front layer to a transmission surface of the front layer, the transmission surface includes a linear incline that is oriented transverse to the base surface such that the front layer has a wedge shape;
  mounting the front layer to a plurality of acoustic stacks such that the base surface faces the acoustic stacks and the transmission surface faces away from the acoustic stacks, wherein the acoustic stacks are configured to generate ultrasound signals refract through the front layer and are emitted from the transmission surface; and
  enclosing the front layer and the acoustic stacks within a housing of an ultrasound probe.

* * * * *